United States Patent
Woolard et al.

(10) Patent No.: US 6,500,618 B1
(45) Date of Patent: Dec. 31, 2002

(54) METHODS AND APPARATUS FOR DETECTING LESION-INDUCED RESONANCES IN DEOXYRIBONUCLEIC ACID VIA MILLIMETER OR SUBMILLIMETER WAVE SPECTROSCOPY

(75) Inventors: Dwight L. Woolard, Raleigh, NC (US); James O. Jensen, Bel Air, MD (US); William R. Loerop, Aberdeen, MD (US); David L. Rhodes, Brick, NJ (US); Hong-Liang Cui, East Brunswick, NJ (US); Janet L. Jensen, Bel Air, MD (US); Alan C. Samuels, Havre de Grace, MD (US); Thomas Koscica, Clark, NJ (US); Harry Salem, Bel Air, MD (US)

(73) Assignees: Trustees of Stevens Institute of Technology, Hoboken, NJ (US); The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/601,412

(22) PCT Filed: Feb. 1, 1999

(86) PCT No.: PCT/US99/02158

§ 371 (c)(1),
(2), (4) Date: Oct. 6, 2000

(87) PCT Pub. No.: WO99/39008

PCT Pub. Date: Aug. 5, 1999

Related U.S. Application Data

(60) Provisional application No. 60/073,403, filed on Feb. 2, 1998.

(51) Int. Cl.$^7$ .............................. C12Q 1/68; G01J 3/02
(52) U.S. Cl. .................. 435/6; 250/339.07; 250/339.12
(58) Field of Search ........................ 435/6; 250/339.07, 250/339.12

(56) References Cited

PUBLICATIONS

Webb et al (1971) Science 174:72–74.*

Woolard, et al., "Millimeter Wave–induced Vibration Modes in DNA as a Possible Alternative to Animal Tests to Probe for Carcinogenic Mutations", *J. Applied Toxicology*, 1997, 18, 4:243–246.

Belyaev., et al., "Resonance effect of millimeter waves in the power range from 10(–19) to 3 X 10 (–3) W/cm2 on *Escherichia coli* cells at different concentrations", Bioelectromagnetics 1996, 17:312–321.

* cited by examiner

*Primary Examiner*—Remy Yucel
*Assistant Examiner*—Bronwen M. Loeb
(74) *Attorney, Agent, or Firm*—Licata & Tyrrell P.C.

(57) ABSTRACT

Methods and apparatus for measuring the millimeter or submillimeter wave absorption spectra in a sample of DNA molecules are provided.

2 Claims, 3 Drawing Sheets

METHODS AND APPARATUS FOR DETECTING LESION-INDUCED RESONANCES IN DEOXYRIBONUCLEIC ACID VIA MILLIMETER OR SUBMILLIMETER WAVE SPECTROSCOPY

This application claims the benefit of U.S. Provisional Application No. 60/073,403, filed Feb. 2, 1998.

INTRODUCTION

This invention is owned in part by the United States of America as represented by the Secretary of the Army. Accordingly, the U.S. Government may have certain rights in this invention.

FIELD OF THE INVENTION

The presence of phonon phenomena induced in DNA by radiation in the 75 GHz to 5 THz frequency range have now been demonstrated to result in resonance absorption properties unique to a particular DNA molecule. The present invention relates to a method and apparatus for measuring the phonon resonance occurring in a DNA molecule when the molecule is subjected to electromagnetic radiation in the 75 GHz through 5 THz frequency range. The method and apparatus of the present invention are useful in locating and identifying DNA molecules of interest and in determining damage to known DNA samples.

BACKGROUND OF THE INVENTION

The genetic molecule deoxyribonucleic acid (DNA) is constantly exposed to a variety of chemical and physical agents resulting in changes to the structure of this molecule. These changes in the structure of the DNA molecule can interfere with replication and transcription of DNA and are generally referred to as DNA damage. Biological consequences of DNA damage include cell death and mutations, events that may cause cancers, mental retardation and reduced growth and development.

Various methods exist for detecting DNA damage. For example, photodamage in DNA resulting from ultraviolet radiation can be detected by chromatography, enzymatic and biochemical incision of DNA at sites of photoproducts or antibody binding to structural damage in DNA. The cyclobutane dimer was first detected in DNA using two-dimensional paper chromatography. Other types of base damage can be determined via techniques such as thin-layer chromatography and high pressure liquid chromatography. Other procedures measure strand breaks induced directly in DNA via an agent or via enzymatic or biochemical treatments that cleave DNA at damaged sites. For example uvrABC exinuclease, a partial excision repair complex purified from *Escherichia coli*, cleaves DNA on either side of damage produced by exposure to genotoxic chemicals or ultraviolet radiation. More recently, the ability of endonuclease VII to cleave at mispairings in double-stranded DNA has been exploited for enzymatic mutation detection (Youil et al. Proc. Nat'l Acad. Sci. USA 1995 92:87–9). Further, Golz et al. have disclosed improved reaction conditions which increase the selectivity of endonuclease VII for mismatches up to 500 fold (Mutat. Res. 1998 382(3–4):85–92). Immunochemical approaches adapted to the analysis of DNA damage include immunoassays, immunofluorescence, immunoprecipitation, enzyme-linked radioimmunoassays, and quantitative and immunoelectron microscopy. In addition, an ultrasensitive method for measuring DNA damage was recently described. This method couples immunochemical recognition with capillary electrophoresis and laser-induced fluorescence detection (Le et al. Science 1998 280 30 (5366):1101–2).

However, these methods for detecting DNA damage are indirect and relatively cumbersome. Further, they are not suitable for field detection in a stand-off mode.

Recent advances in understanding the interaction between microwave/millimeter wave radiation and living matter have opened new avenues in the detection and identification of microorganisms. In particular, DNA has been suggested to interact with electromagnetic radiation in the millimeter wave regions of the spectrum, due to the presence of phonon modes and plasmon modes of base pairs along the double helix of the DNA chain (Saxena, V. K. and Van Zandt, L. L. Phys. Rev. A 1989 40:6134; Saxena et al. Phys. Rev. A 1989 39: 1474; Van Zandt, L. L. and Saxena, V. K. Phys. Rev. A 1990 42:4993; Saxena, V. K. and Van Zandt, L. L. Phys. Rev. A 1992 45:7610; and Smith et al. IEEE J. Quantum Elec. 1988 15 24:255).

A modified self-consistent phonon approximation theory has been used to calculate temperature dependent interbase hydrogen bond disruption profiles for a number of six base pair repeating sequence infinite B-DNA polymers with various guanine-cytosine/adenine-thymine ratios (Chen, Y. Z. and Prohofsky, E. W. Eur. Biophys. J. 1996 25(1):9–18). Calculations via this modified phonon approximation theory were used effectively to calculate H-bond disruption behavior of different DNA sequences.

The expected absorption of microwave radiation in the GHz frequency range by fixed-length DNA polymer molecules dissolved in saline solution have also been calculated (Biopolymers 1989 28(8):1429–33).

Further, the feasibility of using spectroscopic techniques, and more specifically microwave and millimeter wave technology, as a probe for possible detection of damage to DNA has been examined by Woolard et al. (J. Of Applied Toxicology 1997 17(4):243–246). In this study, a series of resonances were first predicted, based on available physical parameter values and reasonable assumptions, in a spectral region with a frequency at 88, 89, 110, 172, 232, 300, 382, 418, 503, 561, 638, 784, 891, 920 and 1019 GHz. Preliminary experiments were then conducted to detect some of the resonances using microwave absorption spectroscopy. More specifically, DNA samples from relatively similar species, salmon and herring, were mechanically loaded as dry DNA salts into a 100-mil long shortened section of waveguide and microwave scattering parameter ($S_{11}$) data was generated via an HP 8510 W-band (i.e. 85–110 GHz) tester. A variance in the occurrence of resonance behavior as a function of electromagnetic energy frequency between the DNA samples of the different species was observed. Microwave absorption spectrum of the same dry sodium herring DNA sample in the frequency region of 180–220 GHz were also measured via a Millitech frequency domain-up conversion unit transmitted through a 75-mil section of DNA contained within a Teflon sample holder. Measurements of the dry sodium herring DNA sample were also taken over a much broader frequency range utilizing a Bell Labs T-Ray Source (Smith et al. IEEE J. Quantum Elec. 1988 24:255; Nuss, M. C. IEEE Circuits Devices March, 1996 25). While unconfirmed by any additional measurements, power-absorption results, for transmission through four different locations of the sample layer in the frequency of 100–400 GHz, were disclosed to result in relatively well-defined peaks resolved at 160, 180, 230, 260, 30 290, 330 and 390 GHz. Based upon these preliminary experiments, it is speculated that microwave absorptions techniques may be useful in detecting DNA-based microorganisms. Further, the feasibility and advantages of using a particular set of modes of the DNA polymers as identification resonances are discussed. However, dry-packing of samples into the waveguide sections as described can lead to inhomogeneity of the sample or possible influence by waveguide eigen-modes. Alternatively, measurement of the samples as thick films can lead to standing waves that tend to mask the signal being detected.

In the present invention a method for inducing and detecting lesion-induced resonance phenomena in thin films of a few micrometers or other samples of DNA molecules via an apparatus comprising an electronically tunable source of electromagnetic radiation capable of generating a broad range of frequencies in the millimeter and submillimeter range wave spectral region, a cavity or sample holder containing the DNA sample and a detector capable of monitoring and recording the radiant power transmitted through the sample as a function of frequency is provided.

SUMMARY OF THE INVENTION

An object of the present invention is to provide a method of identifying an unknown DNA molecule in a sample which comprises transmitting through a sample of unknown DNA electromagnetic radiation in a selected range of frequencies in the millimeter or submillimeter wave range; detecting the radiation transmitted through the sample over the selected range; generating an absorbance spectrum which correlates with the detected radiation; and comparing the generated absorbance spectrum with absorbance spectra generated for known DNA samples so that the unknown DNA molecule is identified.

Another object of the present invention is to provide a method of detecting a mutated DNA molecule from a selected species which comprises transmitting through a sample of DNA electromagnetic radiation in a selected range of frequencies in the millimeter or submillimeter wave range; detecting the radiation transmitted through the sample over the selected range; generating an absorbance spectrum which correlates with the detected radiation; and comparing the generated absorbance spectrum with absorbance spectra generated for nonmutated DNA of the same species wherein differences in the absorbance spectra are indicative of a mutation.

Another object of the present invention is to provide a method of identifying agents which mutate DNA which comprises transmitting through a first sample of DNA electromagnetic radiation in a selected range of frequencies in the millimeter or submillimeter wave range; detecting the radiation transmitted through the first sample of DNA over the selected range; generating an absorbance spectrum which correlates with the detected radiation; contacting the first sample of DNA sample with an agent suspected of mutating DNA; transmitting through the DNA sample contacted with the agent electromagnetic radiation in a same selected range of frequencies in the millimeter or submillimeter wave range as the first sample of DNA; detecting the radiation transmitted through the DNA sample contacted with the agent over the selected range; generating an absorbance spectrum which correlates with the detected radiation for the DNA sample contacted with the agent; and comparing the absorbance spectrum of the first DNA sample to the absorbance spectrum of the DNA sample contacted with the agent wherein differences in the absorbance spectra are indicative of the agent being mutagenic.

Yet another object of the present invention is to provide an apparatus for identifying a DNA molecule which comprises a spectrometer composed of a broadband millimeter or submillimeter wave signal source and a detector, a data bank with all spectra of defect-related DNA local modes for a class of substances, and a means for comparing spectra obtained with spectra in the data bank.

DETAILED DESCRIPTION OF THE INVENTION

Figure 1:
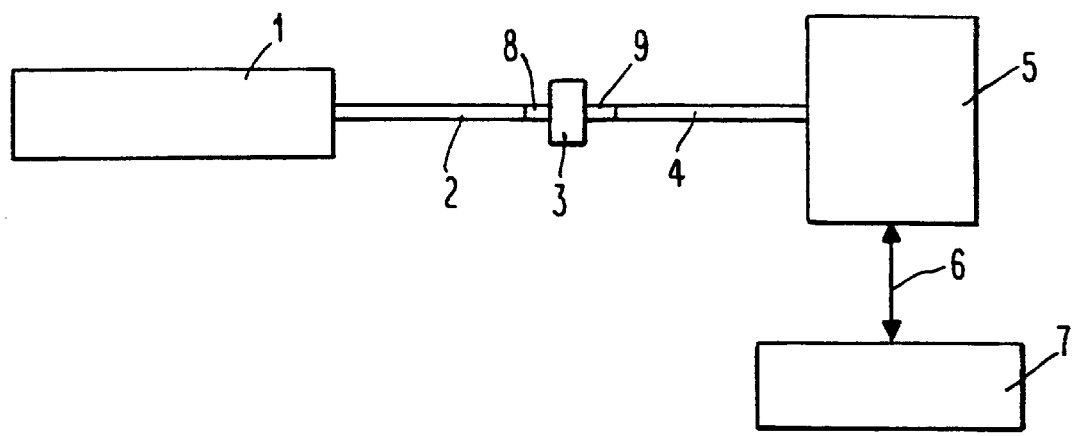
FIG. 1 provides a schematic of a notional apparatus for measuring the absorption spectra of DNA samples useful in the method of the present invention.

Until recently, the 80 GHz to 1000 GHz region of the electromagnetic spectra has been difficult to observe spectrally due to the lack of adequate sources and reliable detectors. Spectral features for DNA polymers predicted by theoretical studies arise primarily from localized motions, spread over one or more base-pair units. Based upon available physical parameter values and reasonable assumption, a series of resonances have been predicted in the spectral region and include 88, 89, 110, 172, 232, 300, 382, 418, 503, 561, 638, 784, 891, 920 and 1019 GHz (Edwards et al. Phys. Rev. Lett. 1984 53:1284 and Van Zandt, L. L. and Saxena, V. K. 1994 K. Biomol. Struc. Dyn. 1994 11:1149). Detailed descriptions, however, depend upon the strength of van der Waals interactions, electron exchange interactions, Coulombic interactions and hydrogen bonding. Thus, prior predictions merely serve as a guide insofar as some of the parameters are not known exactly and, more importantly, the theories are model dependent and may not be completely accurate.

Techniques have only recently become available for spectroscopic studies of this nature (Smith et al. IEEE J. Quantum Elec. 1988 24:255 and Nuss, M. C. IEEE Circuits and Devices, Mar. 25, 1996). Using these techniques, however, phonon modes of various DNA polymers have now been observed and identified.

The present invention relates to a method and apparatus for applying this technique in detecting DNA samples in the millimeter or submillimeter wave regime. This technique is based on the millimeter or submillimeter wave absorption measurement of DNA samples, which shows prominent spectral features corresponding to local vibrational modes of the DNA chains, due to natural lesions induced, for example, by broken or stretched (weakened) hydrogen bonds, missing or additional atomic groups or dimers, or substitutional impurities. Various DNA samples including, but not limited to, thin film of a few micrometers, solids, liquids and aerosols can be measured via the method of the present invention. The ability to measure DNA samples in various forms provides the method with flexibility in varying the density of particles and particle size of the samples. Samples may comprise a single purified DNA molecule, several types of DNA molecules or a mixture of DNA and other molecules.

In general, a resonance trace or spectrum of a DNA sample as a function of frequency is generated via a suitable radiation source, a sample holder for the DNA and a detector. More specifically, to generate such a spectrum, a DNA sample is subjected to a tunable source of radiation in the 75 GHz through 5 THz frequency range or a portion thereof, and the power of the transmitted radiation is monitored as a function of input frequency. The method is performed in a suitable apparatus containing a blank or empty sample holder to establish a baseline frequency dependent power distribution of the apparatus. The sample is then introduced to the sample holder and the procedure repeated to generate a resonance trace or spectrum of the phonon modes in the DNA molecules in the sample. When a given frequency of radiation induces a phonon mode in the DNA molecule, the molecule will absorb radiation, resulting in attenuation of the transmitted power of the frequency. Because the phonon mode is essentially an acoustic phenomena, the resonance is expected and shown to occur over a fairly broad frequency region of the order of several GHZ. The resultant trace of transmitted power as a function of the frequency of the applied radiation is dependent upon the macroscopic structure of the DNA molecules under study; and is therefore a characteristic of the nature and condition of the molecule.

A schematic diagram of a notional apparatus useful in the method of the present invention is shown in FIG. 1. Actual dimensions and geometric arrangement of the depicted components may vary from this diagram as required to accommodate the variety of sources and detection technologies which can be incorporated into this apparatus. In general, however, the apparatus comprises a millimeter or sub-millimeter tunable radiation source 1. Examples of such sources include, but are not limited to, klystrons, backward wave oscillators, GUN diodes, IMPATT diodes, quantum well diodes, photomixers, frequency multipliers, Fabry-Perot resonance cavities or any other suitable technology having the capacity to generate and tune electromagnetic radiation in the frequency region spanning from 75 GHz to 5 THz. Depending upon the nature and principle of operation of the chosen source, ancillary equipment such as amplifiers, phase locking circuitry, oscillators, modulators and choppers may also be incorporated into the apparatus for successful operation. The apparatus also comprises a transmitting waveguide or channel 2 through which radiation is transmitted to the sample. The sample is contained in a sample cell 3. The sample cell 3 may be as simple as a free space cell in which radiation is transmitted from the transmitting waveguide 2 through a first cone 8 and through the sample which is collected in a second cone 9 by a receiving waveguide 4. However, more elaborate sample cells such as cavity waveguides, in which the dimensions of the cavity are tailored such that standing resonant waves form in the cavity and interact with the sample, can also be used. A Hughes-Wilson Stark cell may also be employed. In one embodiment, the sample is contained within the sample cell in the form of a thin layer perpendicular to the direction of propagation of electromagnetic energy. The thin layer may be clad by supporting layers of an inert material which is transparent in these regions, or it may be a monolayer or multilayers supported on a transparent substrate. The receiving waveguide 4 carries the transmitted signal to the detector 5. Typically, the detector 5 is a diode, preferably a more sophisticated diode detection technology such as a Shottky diode multiplier chain. In some embodiments, the radiation source 1 is pulsed and the detector 5 is gated. In this embodiment, the detector gate frequency is swept relative to the source pulse to acquire a time-domain sample of the pulse. The detector 5 is connected to a means for data output and storage 7 via a recording or digitizing circuit 6. Examples of means for data output and storage include, but are not limited to, chart recorders, plotters and digital computers.

The absorption coefficient $\alpha(v)$ of the sample as a function of frequency $v$ can be determined from the transmission measurements. It can be expressed as $$\alpha(v) = \frac{1}{l} \ln\left(\frac{P_1(v)}{P_2(v)}\right),$$

where $P_1(v)$ is the power measured by the detector without the sample and $P_2(v)$ is the power measured by the detector with the sample. l is the pathlength of the signal through the sample.

Figure 2:
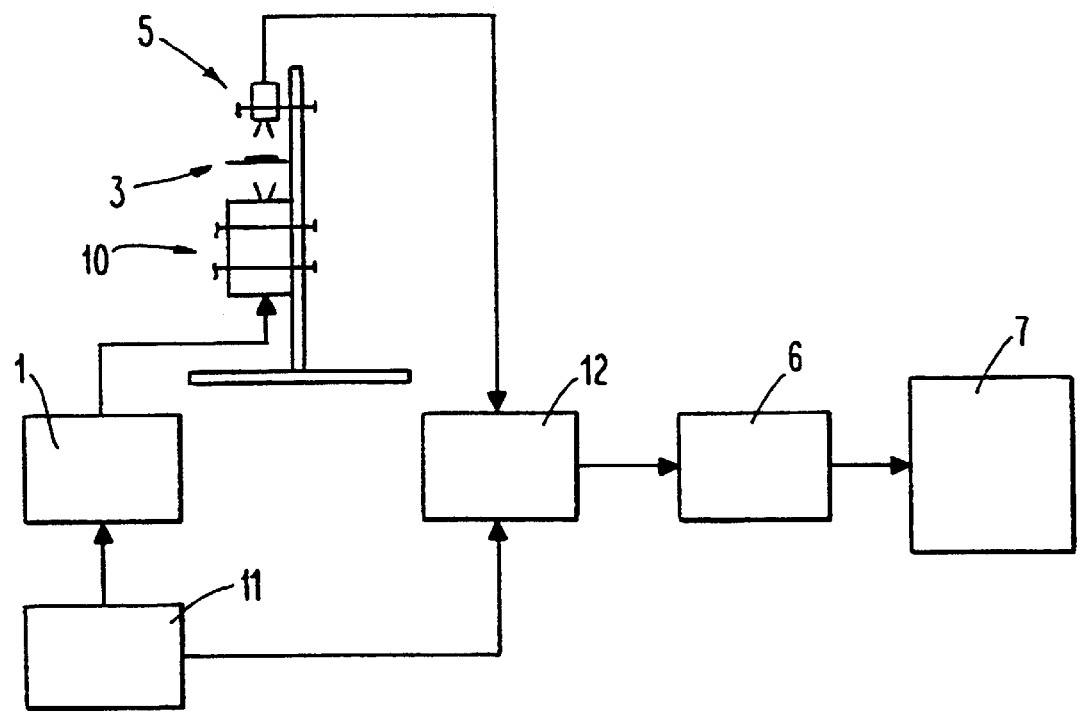
FIG. 2 provides a block diagram of one embodiment of an apparatus for measuring the absorption spectra of DNA samples wherein the sample is subjected to a single beam of radiation.

FIG. 2 shows a block diagram of one embodiment of an apparatus for measuring the absorption spectra of DNA samples. As depicted in FIG. 2, the DNA sample is placed on a thin film support which serves as the sample holder or cell 3 below an RF detector 5 and above a multiplier 10 connected to an RF source 1 and an electronic chopper 11. The multiplier 10 works along with the source to up-convert the frequency from microwave to millimeter/submillimeter waves. The electronic chopper 11 provides a timing mechanism for synchronous output and detection. In this embodiment, the RF detector 5 and the synchronous detector 12 work together to detect the absorbance spectra. Transmission from the RF detector 5 and synchronous detector 12 is then sent to a digitizer or digitizing circuit 6. The digitizer or digitizing circuit 6 converts the analog signal output from the detector to a digital signal so that a PC data processing system 7 can analyze and store it as a data file. Using this embodiment, the absorption spectra of salmon, herring and spore DNA were determined. The absorption spectra of the fish samples were clearly distinguishable from the absorption spectra of the spore as the fish samples each had three distinctive peaks in the observed frequencies while the spore sample only had two. Further, frequency shifts of the absorption peaks for salmon and herring made these spectra from similar species also distinguishable.

Figure 3A:
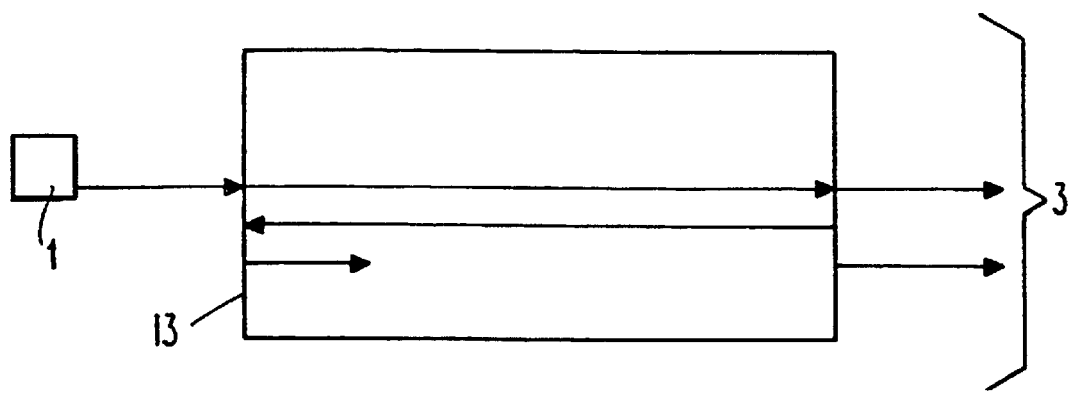
FIG. 3 provides a diagram of an exemplary sample holder useful in measuring particular DNA samples. As depicted in FIG. 3B, it is preferred that the walls of the sample holder box be tilted to eliminate multiple paths as depicted in FIG. 3A which can lead to spatial harmonics in the detected signal that mask the true features of the spectra.
Figure 3B:
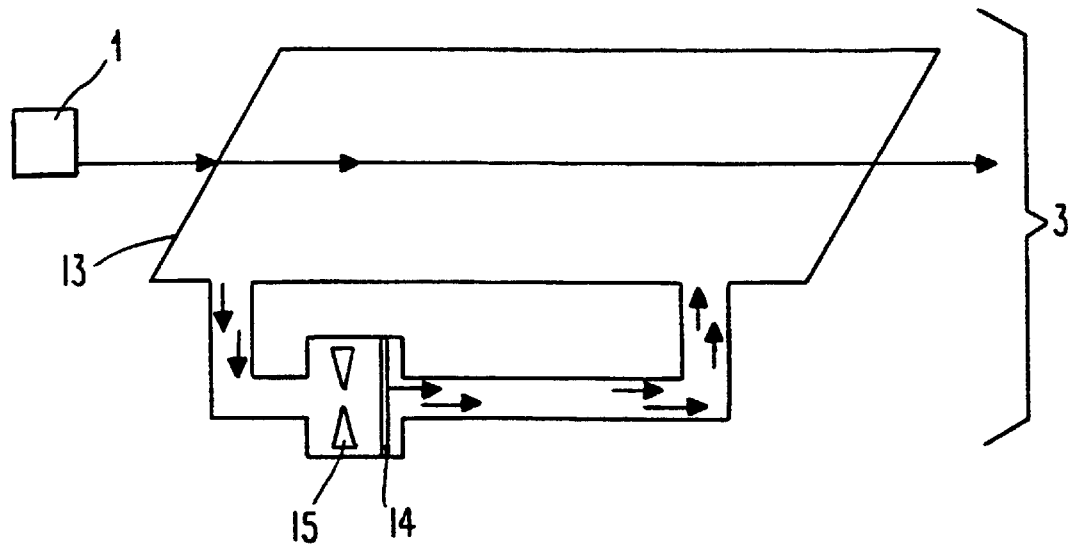

In another embodiment, the method of the present invention may be used in detecting aerosolized samples. The samples will generally be prepared from powders. Preparation of samples as aerosols affords flexibility for varying concentrations and particle size. FIG. 3 provides a diagram of an embodiment of a sample cell or holder 3 useful in measuring aerosolized samples. In this embodiment, other elements of the apparatus remain the same. As depicted in FIG. 3B, the walls 13 of the sample cell or holder 3 are preferably tilted to eliminate multiple paths as shown in FIG. 3A. Multiple paths lead to spatial harmonics in the detected signal that mask the true features of the spectra. As also depicted in FIG. 3B, the aerosol sample cells is preferably equipped with a micropore filter 14 and a fan 15.

Figure 4:
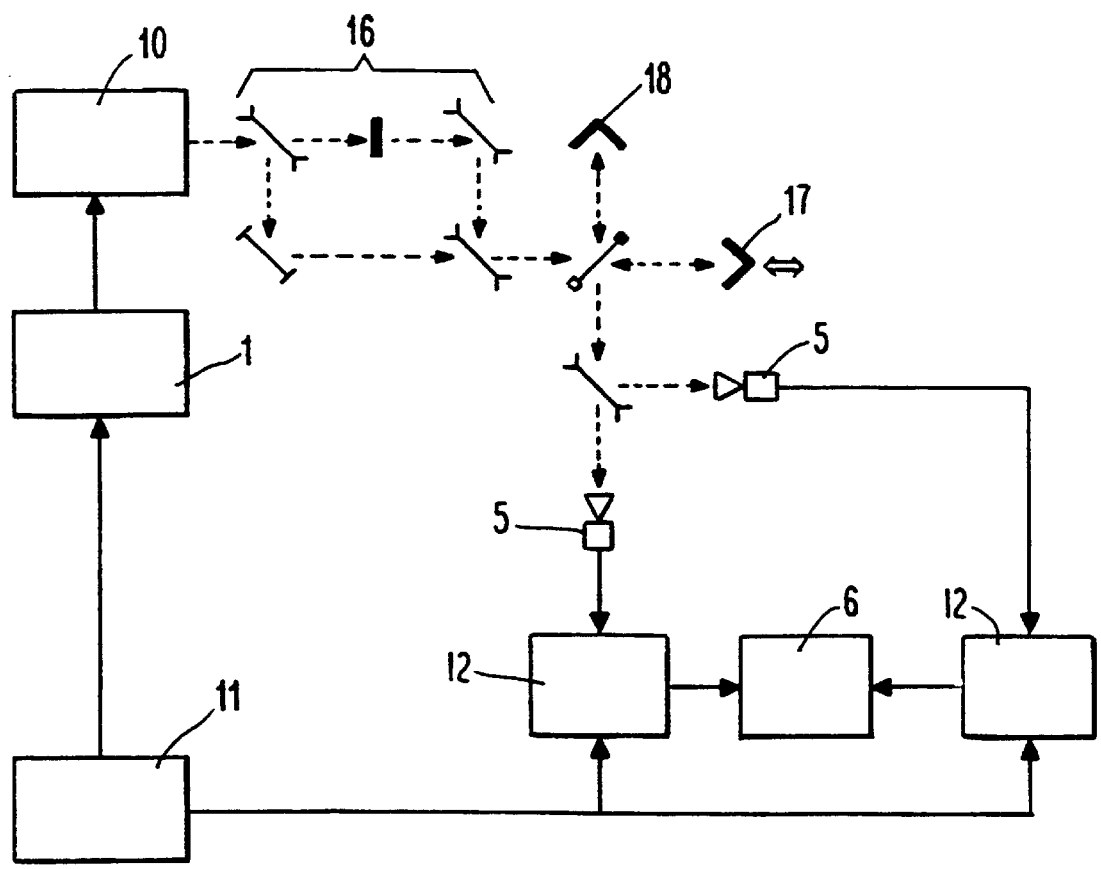
FIG. 4 provides a block diagram of an apparatus for measuring millimeter wave absorbance spectrum using a Martin-Puplett interferometer.

In yet another embodiment, as depicted in FIG. 4, a more sophisticated detection system is utilized. This system relies on an interferometry set-up known as the Martin-Puplett interferometer (Martin, D. H., Polarizing interferometric spectrometers for the near- and submillimeter spectra, K. J.

Button Ed., Infrared and Millimeter Waves, Academic Press, 1982, Vol. 6, pp. 65–148). The Martin-Puplett interferometer is a polarizing version of the Michelson interferometer. As depicted in FIG. 4, the incoming signal from the RF source 1 and multiplier 10 is split by a wire grid polarizer 16 into two equal components which are recombined after being directed along paths of different lengths. The output signal is therefore modified in a way that depends upon the path difference and signal wavelength. In the single beam determination of the attenuation of transmission through a sample, the fractional reduction in the beam intensity is obtained by the difference between the sample in the absence and presence of the beam. A double-beam determination, however, can measure the difference directly. For the four ports of a Martin-Puplett Interferometer, the two input beams are transmitted by and reflected from the polarizer 16 and orthogonally polarized. Signal power enters an interferometer in both input ports. One detector 5 has the power $$\frac{1}{2}(I_1 + I_2) + \frac{1}{2}(I_1 - I_2)\cos\Delta,$$

the other 5

$$\frac{1}{2}(I_1 + I_2) - \frac{1}{2}(I_1 - I_2)\cos\Delta$$

where $I_1$ and $I_2$ are the intensities of the signal exiting the two arms of the Mach-Zehnder interferometer on the input side, $\Delta = 2\Pi\chi/\lambda$ is the total phase difference of the two beams, $\chi$ is the path difference of the two beams, and $\lambda$ is the wavelength of the input signal. The unmodulated component ½ $(I_1+I_2)$ contains no spectral information but it can carry noise, thus it is important to note that this component can be suppressed by recording the difference between the powers in the two output beams, that is $(I_1-I_2)\cos\Delta$. The absorbed intensity by the sample is directly proportional to this latter quantity, which can be accurately measured. In the embodiment, the phase factor may also be adjusted via the mobile roof mirror 17 and fixed roof mirror 18 so that the cosine factor can be set to a magnitude of 1.

The method and apparatus of the present invention have a variety of uses only a few of which are described in detail. In one embodiment, a high sensitivity system for detecting absorption spectra and classifying unknown samples is useful in the rapid detection and identification of microorganisms. Such high sensitivity systems are essential in biological defense. Traditionally, such detection is mostly based upon optical techniques such as infra-red scattering, ultraviolet fluorescence, IR absorption and resonance Raman scattering (Carrieri et al. Chemical Research Development and Engineering Center technical Report, CRDEC-TR-87084, 1987; Lakowicz, J. R. Principles of Fluorescence Spectroscopy, Plenum Press, New York, 1983; Helm et al. J. General Microbiology 1991 137:69; and Manoharan et al. J. Microbiol. Meth. 1990 311:1). An attractive feature of optical techniques for identification of microorganisms is that they can be used in a standoff mode, where the sample is examined remotely and does not have to be extracted from the environment. This offers many operational advantages for a field-type instrument. However, the technical challenges in developing a field instrument based on one of these optical techniques is formidable.

Using the method of the present invention, however, a working field detector for identifying DNA can comprise a spectrometer composed of a broadband millimeter or submillimeter wave signal source and a detector, a data bank with all spectra of defect-related DNA local modes for a class of substances, and a means for comparing the spectra obtained with spectra in the databank. Spectra in the databank preferably comprise information gathered from systematic experiments and is supplemented with numerical computations.

In this method, an unknown DNA molecule in a sample is identified by transmitting through the sample electromagnetic radiation in a selected range of frequencies in the millimeter or submillimeter wave range. By "selected range of frequencies" it is meant a range of frequencies between 75 GHz and 5 THz. Radiation transmitted through the sample over the selected range of frequencies is detected and an absorbance spectrum correlating with the detected radiation is generated. The generated absorbance spectrum for the unknown DNA sample is then compared with absorbance spectra generated for known DNA samples so that the unknown DNA molecule is identified.

A quantitative means for implementing a comparison and matching procedure is outlined below. Let S be the vector representing the scores for a sample being tested against all samples in the library. Let M be a matrix containing features of all samples with each row of M normalized to 1. Further, let D be the vector of measured features for an unknown sample. The components of D are either 0 or 1. For example, the nth component being 0 means the nth feature is absent, whereas it being 1 means the feature is present. Thus, S=M*D, whose components can be taken as the probability of matching the corresponding library entry.

The method of the present invention is also useful in detecting a mutated DNA molecule from a selected species. Detection of mutations is of particular importance in the diagnosis of genetic based diseases. In this embodiment, electromagnetic radiation in a selected range of frequencies in the millimeter wave range can be transmitted through a DNA sample obtained from a biological sample, i.e. blood, urine or spinal fluid of an individual suspected of suffering from a genetic based disease. Radiation transmitted through the sample over the selected range is detected and an absorbance spectrum correlating with the detected radiation is then generated. The generated absorbance spectrum is then compared to absorbance spectra generated for DNA samples from individuals known not to carry the mutation. Differences in the absorbance spectra are indicative of a mutation. As will be obvious to those of skill in the art upon this disclosure, identification of mutated DNA is also useful in the development of new cell lines and transgenic animals for use as disease models.

The method of the present invention is also useful in identifying agents which mutate DNA. In this embodiment, an absorbance spectrum is generated as described above for a first sample of DNA. This DNA sample is then contacted with an agent suspected of mutating DNA and a second absorbance spectrum for the DNA sample contacted with the agent is generated. The absorbance spectrum of the first DNA sample then compared to the second absorbance spectrum for the DNA sample contacted with the agent. Differences in the absorbance spectra are indicative of the agent being mutagenic.

What is claimed is:

1. A method for generating absorbance spectra useful in distinguishing different DNA molecules comprising:
   (a) transmitting through a sample of DNA electromagnetic radiation in a 75 GHz to 5 THz frequency range;
   (b) detecting the radiation transmitted through the sample over the 75 GHz to 5 THz frequency range; and
   (c) generating an absorbance spectrum which correlates with the detected radiation and which can be used to distinguish different DNA molecules.

2. An apparatus for generating absorbance spectra useful in distinguishing DNA molecules from different species comprising:
(a) a millimeter or sub-millimeter tunable radiation source delivering radiation in a 75 GHz to 5 THz frequency range;
(b) a transmitting waveguide or channel through which radiation is transmitted from the millimeter or sub-millimeter tunable radiation source to a DNA sample;
(c) a sample cell for holding the DNA sample;
(d) a receiving waveguide which carries the radiation signal transmitted through the DNA in the sample cell to a detector;
(e) a detector of the transmitted radiation signal which detects radiation in the 75 to 5 THz frequency range; and
(f) a means for data output and storage for generation of the spectra of the DNA sample, said means connected to the detector via a recording or digitizing circuit.

* * * * *